| United States Patent [19] | [11] Patent Number: 4,857,045 |
| --- | --- |
| Rydell | [45] Date of Patent: Aug. 15, 1989 |

[54] ATHERECTOMY CATHETER

[75] Inventor: Mark A. Rydell, Golden Valley, Minn.

[73] Assignee: Schneider (USA) Inc., A Pfizer Company, Minneapolis, Minn.

[21] Appl. No.: 111,715

[22] Filed: Oct. 23, 1987

Related U.S. Application Data

[63] Continuation-in-part of Ser. No. 44,357, Apr. 30, 1987, abandoned.

[51] Int. Cl.⁴ .............................................. A61B 17/32
[52] U.S. Cl. ...................................... 604/22; 128/305
[58] Field of Search ................ 128/304, 305, 751-755; 604/22, 52, 53, 27, 35, 43; 30/276

[56] References Cited

U.S. PATENT DOCUMENTS

| 4,167,943 | 9/1979 | Banko | 604/22 |
| 4,167,944 | 9/1979 | Banko | 604/22 |
| 4,203,444 | 5/1980 | Bonnell et al. | 128/305 |
| 4,445,509 | 5/1984 | Auth | 128/305 |
| 4,589,412 | 5/1986 | Kensey | 604/22 |
| 4,631,052 | 12/1986 | Kensey | 604/22 |
| 4,681,106 | 7/1987 | Kensey et al. | 604/22 |
| 4,686,982 | 8/1987 | Nash | 128/305 |
| 4,696,667 | 9/1987 | Masch | 604/22 |
| 4,732,154 | 3/1988 | Shiber | 128/305 |

Primary Examiner—Michael H. Thaler
Assistant Examiner—William W. Lewis
Attorney, Agent, or Firm—Orrin M. Haugen; Thomas J. Nikolai; Frederick W. Niebuhr

[57] ABSTRACT

A catheter for facilitating the restoration of patency to a blood vessel occluded with an atheroma or other similar lesion or thrombus comprising an outer flexible plastic tubular member having a plurality of ports proximate its distal end and concentrically surrounding an inner flexible plastic tubular member having a cutting loop at its distal end. The distal end portion of the inner tubular member is journaled for rotation in the distal end portion of the outer tubular member. A motor is provided at the proximal end of the catheter assembly for rotatably driving the inner tubular member and the cutting loop thereof while flushing the treatment site and aspirating the flushing liquid, blood and any debris loosened during the procedure.

9 Claims, 2 Drawing Sheets

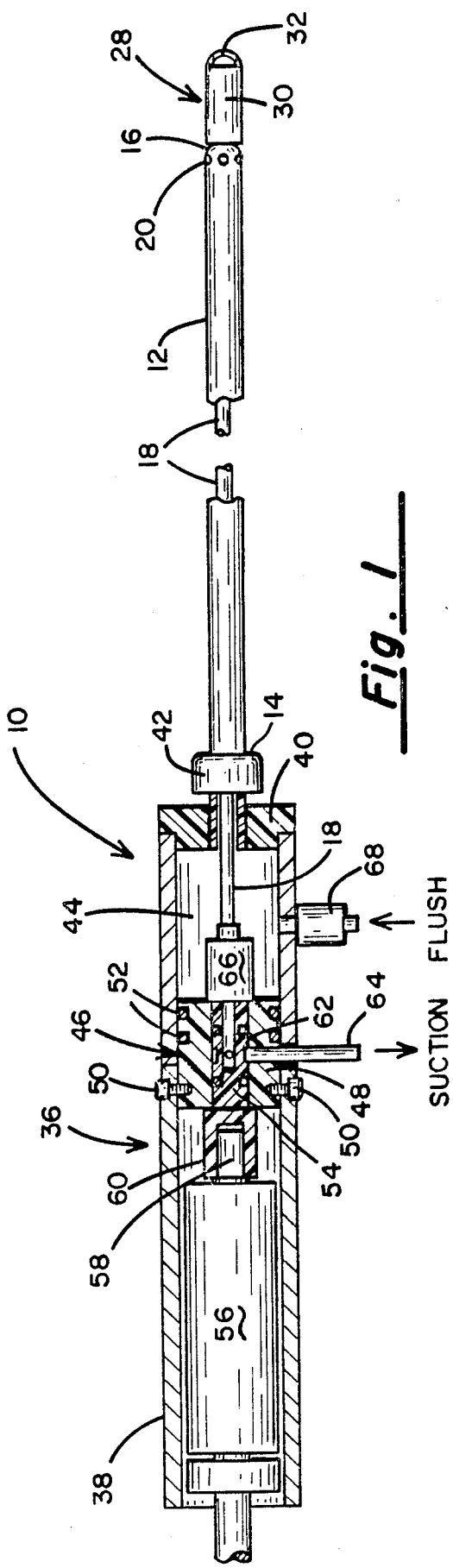
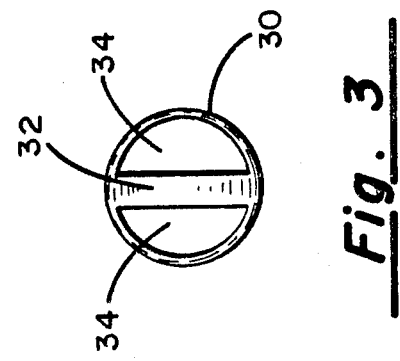
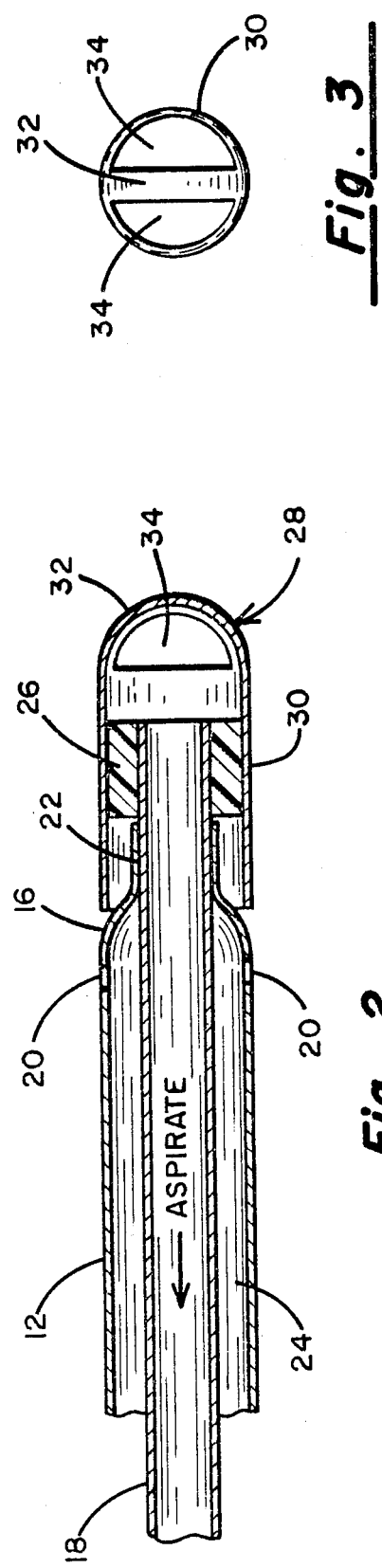

ATHERECTOMY CATHETER

CROSS REFERENCE TO RELATED APPLICATIONS

This application is a Continuation-in-Part of Application Ser. No. 07/044,357, filed Apr. 30, 1987, and entitled ATHERECTOMY CATHETER (now abandoned).

BACKGROUND OF THE INVENTION

I. Field of the Invention

This invention relates generally to intravascular catheters, and more particularly to the design of an atherectomy catheter useful in restoring patency to a blood vessel that is blocked or partially blocked by atheromas or other form of stenotic or thrombotic lesion.

II. Discussion of the Prior Art

The build-up of atheromas or the formation of thrombi in a blood vessel can cause serious circulatory problems and when complete blockages occur, distal tissues may be deprived of oxygen and nutrients leading to death of those cells distally of the blockage. Thus, the formation of an atheroma in a coronary artery can lead to a coronary infarction, especially when the artery becomes so narrowed by the plaque build-up that a tiny clot or thrombus cannot pass. Similarly, an atheroma or other type of stenotic lesion in a peripheral vein or artery can have a corresponding affect on tissue and cells supplied by the blocked blood vessel.

The treatment of such a condition naturally depends upon the location or site of the blockage. In the case of a blocked or partially blocked coronary artery, it has been the practice to conduct open-heart surgery wherein the blocked vessel is by-passed with an autograft. Similarly, blood vessel shunts have been installed in other body areas as well. Such surgery, however, tends to be quite traumatic involving opening the patient's chest and pericardium in the case of coronary by-pass surgery or extensive excision and vessel replacement in the case of other peripheral blockages.

More recently, following the technique credited to A. Grunzig, a balloon catheter may be used to restore patency to a blood vessel without extensive surgery. A catheter having a small inflatable balloon on its distal end may be routed through the vascular system to the site of the constriction or blockage and when the deflated balloon is appropriately positioned to span the blockage, a fluid may be introduced into the proximal end of the catheter to inflate the balloon to a sufficiently high pressure whereby the blockage may be spread open and patency restored.

As is pointed out in the Auth U.S. Pat. No. 4,445,509, there are certain deficiencies in the Grunzig procedure which render it ineffective in certain applications. For example, the blockage may be such that it is not possible to safely force the distal tip of the catheter through the blockage prior to the inflation of the balloon. In such a situation it would be desirable if one could safely "tunnel" through the blockage using an appropriate cutting tool. Once a passage has been formed during such tunneling operation, a balloon can be advanced into the occlusion until it is totally across it. Once so positioned, the balloon can then be inflated and the angioplasty procedure completed.

SUMMARY OF THE INVENTION

In accordance with the present invention, there is provided an atherectomy catheter comprised of two concentrically disposed elongated, flexible tubular members having respective inside and outside measurements allowing a sufficient clearance between the two whereby fluid may be perfused through the lumen of the outer tubular member and out through one or more ports formed through the wall of the outer tubular member near its distal end. The distal end portion of the outer tubular member is necked down so as to be of a lesser exterior dimension than the remaining portion of that outer tubular member. The inside diameter of the outer tubular member in this necked down portion conforms closely to the outside diameter of the inner tubular member and, in fact, provides a journal or bearing surface for the inner tubular member when it is rotated. Secured to the distal tip portion of the inner tubular member is a cutter member which includes an outer tubular portion surrounding the distal end of the outer tubular member. It has a radially disposed arcuate loop projecting longitudinally outward from the distal end of the tubular body portion of the cutter member.

Secured to the proximal end of the catheter assembly is a drive means which is configured to rotate the inner tubular member relative to the outer tubular member while allowing the simultaneous perfusion of a liquid through the outer tubular member and the aspiration of fluids through the lumen of the inner tubular member. In this fashion, upon insertion of the catheter within the patient's vascular system and advancing the distal tip portion thereof to the site of the lesion to be excised, the site can be flooded with a flushing liquid and when the cutter is driven at high speed and advanced into the lesion, the fluids and debris sectioned from the lesion can be aspirated through the lumen of the inner tubular member and collected in a suitable vessel at the proximal end of the assembly. By driving the cutter at a relatively high speed, e.g., 30,000 rpm, the cutter, as configured, finely divides the fatty lesion and effectively liquifies the material prior to its being aspirated back through the lumen of the cutter tube.

OBJECTS

It is accordingly a principal object of the present invention to provide an improved apparatus and technique for treating vascular atheromas.

Another object of the invention is to provide a catheter assembly including an outer elongated flexible tubular member and a concentrically disposed, loosely fitting elongated inner tubular member, the inner tubular member being provided with a cutter attachment at its distal end and adapted to be driven by a drive means disposed at the proximal end of the catheter assembly.

Yet another object of the invention is to provide an atherectomy catheter in which a rotatable cutter is disposed at the distal end thereof and means are provided at the proximal end for driving the cutter at the high rotational speed while simultaneously injecting a flushing liquid and aspirating the treatment site.

These and other objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE DRAWINGS

FIG. 1 is a partially sectioned view illustrating a preferred embodiment of the present invention;

FIG. 2 is a greatly enlarged view of one cutter head arrangement;

FIG. 3 is an end view of the cutter head of FIG. 2; and

DESCRIPTION OF THE PREFERRED EMBODIMENT

Figure 4:
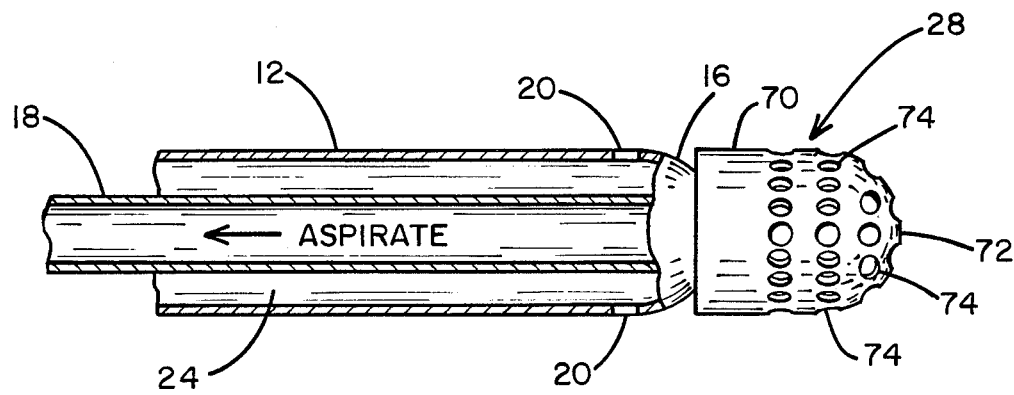
FIG. 4 is a greatly enlarged side elevation of an alternative cutter head arrangement.

Referring to FIG. 1, the surgical device of the present invention is seen to comprise an atherectomy catheter which is indicated generally by numeral 10. It includes an outer elongated, flexible tubular member 12 having a proximal end 14 and a distal end 16. Disposed within the lumen of the outer tubular member 12 is an elongated flexible inner tubular member 18 which extends the full length of the outer tubular member.

Referring to FIG. 2, it can be seen that near the distal end 16 of the outer tube, a series of ports 20 are formed through the wall thereof and it tapers down to a distal end portion 22 which is of a lesser outside diameter than the remaining portion of the catheter body 12. Thus, an annular space 24 is created between the outside diameter of the inner tube 18 and the inside diameter of the outer tube 12. As will be illustrated subsequently, when a liquid is appropriately injected at the proximal end of the catheter assembly, it will profuse through this flush lumen 24 and exit the ports 20.

The outer tubular member in zone 22 conforms to the outside dimension of the inner tubular member 18 and provides a bearing surface for the inner tubular member 18 as it is driven. Adhesively joined to the portion of the inner tubular member 18 which extends distally beyond the end of the outer tubular member 12 is an annular spacer 26 and bonded to the spacer 26 is a cutter head 28.

With reference to FIGS. 1 and 3, one style of cutter head is seen to comprise a generally tubular portion 30, which at least partially surrounds the distal end 16 of the outer tubular member 12, and a radially disposed arcuate loop 32 which projects longitudinally outward from the distal end of the tubular portion 30 of the cutter head 28. The loop effectively divides the open end of the tubular cutter member into a pair of openings 34 through which blood, a flushing liquid, and any tissue debris may be drawn when a vacuum or negative pressure is suitably applied to the proximal end of the inner tubular member 18.

The outer tubular member 12 is preferably extruded from a plastic selected from the group including polyester, nylon and polyolefin. The inner tubular member 18 may also be formed with a like plastic, but with polyester being preferred. The cutter member 28 can be fabricated from either metal or plastic and the overall outside diameter thereof, as well as that of the outer tubular member 12, is determined by the particular location of the atheroma to be treated and the size of the blood vessels leading thereto.

Connected to the proximal end of the outer tubular member is a drive means 36 which, among other functions, is used to rotate the inner tubular member within the lumen of the outer tubular member 12. With reference to FIG. 1, it is seen to include a rigid tubular housing 38 having a plug 40 fitted into the distal end thereof. Extending through a bore formed in the plug 40 is a fitting 42, preferably of the compression type, for joining the outer tubular member 12 to the interior chamber 44 of the tubular housing 38.

Disposed within the housing 38 is a rotary union, indicated generally by numeral 46. It comprises an outer tubular sleeve member 48 fastened to the housing 38 by pins 50. These pins preclude relative rotation between the tubular sleeve 48 and the housing 38. To prevent the flushing liquid from passing from the chamber 44 beyond the rotary union 46, O rings, as at 52, are disposed in annular grooves spanning the tubular sleeve 48. The rotary union further comprises a hollow manifold member 54 which fits within the bore of the outer tubular sleeve 48. This manifold member is dimensioned so as to rotate within that bore when driven by a motor means. In the preferred embodiment, an air motor of the type found in dental drills or the like may be used. Typically, such motors may be designed to rotate at very high speeds, e.g., 30,000 rpm. The shaft 58 of that motor is keyed in a coupling 60 connected to the proximal end of the hollow manifold member 54.

Formed between the outer tubular sleeve 48 and the manifold member contained therein is an annular recess 62 which is ported to the interior of the hollow manifold member. Furthermore, a tubular fitting 64 passes through a bore formed radially through the side wall of the rigid tubular housing 38 and through the wall of the outer tubular sleeve 48 to communicate with that recess 62. The rotatable hollow manifold 54 is also joined to the proximal end of the inner elongated flexible tubular member 18 by a suitable coupler 66.

In use, the elongated catheter assembly is appropriately introduced into the vascular system and advanced until the cutter tip 32 is positioned closely adjacent to the atheroma or other lesion to be excised. Next, a flushing liquid may be introduced through the fitting 68 and into the chamber 44 of the drive means 36. From there, the liquid flows through the lumen of the outer tubular member 12 between its inner wall and the outer wall of the inner tubular member 18. The liquid then exits the ports 20 formed through the side wall of the outer tubular member near its distal end. When a suitable source of negative pressure is applied to the suction fitting 64, the flush liquid along with blood and/or tissue debris, which may be filed from the atheroma, is drawn through the openings 34 formed in the distal end of the cutter 30, through the lumen of the inner tubular member or drive tube 18, and thence through the coupler 66 and into the hollow manifold member 54. The fluid then flows through a port communicating with the annular recess 62 and then out the suction fitting 64 into a suitable receptacle (not shown). At the same time, when the motor means 56 is energized, it drives the hollow manifold member of the rotary union within its tubular sleeve and the drive tube 18 coupled thereto by coupler 66. When the catheter is advanced, and modest pressure is applied between the cutter loop 32 and the tissue being excised, that tissue is finally divided by the rapidly spinning cutter load and washed by blood and flushing liquid through the central lumen of the tube 18 and into the collecting receptacle connected to the suction fitting 64. Once the atheroma has been completely penetrated, blood flow through the blood vessel is restored.

ALTERNATIVE EMBODIMENT

Referring to FIG. 4, there is shown a side elevation of an alternative design for the cutter head 28. As in the embodiment of FIGS. 1 through 3, the cutter head is attached to the distal end of drive tube 18 for rotation therewith. Rather than having a cutting loop 32 effectively defining two aspiration openings 34, the cutting head 28 of FIG. 4 comprises a hollow, bullet-shaped, thin wall sleeve 70 having a hemispherical shaped distal end 72. With no limitation intended, the sleeve 70 may have a thickness of 0.005 inches and a dome radius of 0.050 inches. It may have an overall length on the order of 0.125 inches and can be secured to the end of tube 18 in the same manner as cutter head 30 of FIG. 2.

Formed through the hemispherical end portion of the cutter head of FIG. 4 is a pattern of holes 74. The number of and size of the holes 74 is preferably such that their total area is generally equal to the cross-sectional area of the lumen of the drive tube 18. Also, the diameter of the holes 74 should be two to three times the thickness of the wall of the dome portion 72. For a dome thickness of 0.005 inches, approximately 42 holes, each 0.015 inches in diameter has been found to produce excellent results. Holes 42 are preferably formed in a laser drilling operation. In use, when the drive tube is rotated as previously described, and the cutter head of FIG. 4 is advanced against the atheroma to be excised, the cutter head acts like a grater to finely divide the fatty tissue of the atheroma so that the debris, along with flush liquid and body fluids can be aspirated back through the cutter openings and the lumen of the inner tube 18 to the collection chamber (not shown).

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. A surgical device for excising tissue deposits from the interior of a blood vessel comprising:
   (a) an outer elongated flexible tubular member having an outside diameter which is less than the diameter of the lumen of a blood vessel to be treated and capable of being advanced through said blood vessel lumen without the use of a guidewire, said outer tubular member having a proximal end and a distal end, said distal end having an outside diameter which is less than the outside diameter of the remaining portion of said outer tubular member with said remaining portion of said outer tubular member having at least one fluid passing orifice formed therethrough;
   (b) a single inner elongated flexible tubular member coaxially disposed within said outer tubular member and having a proximal end and a distal end with the outside diameter of said inner tubular member conforming to the inside diameter of said outer tubular member at said distal end of said outer tubular member to journal said inner tubular member for rotation, said distal end of said inner tubular member extending out beyond the distal end of said outer tubular member and axially fixed to be non-translatable relative to said outer tubular member;
   (c) a single-piece cutter member affixed to said distal end of said single inner tubular member, said single-piece cutter member having a tubular proximal portion surrounding the reduced diameter portion of said distal end of said outer tubular member and a dome-shaped distal end portion, the outside diameter of said tubular portion of said cutter member being generally equal to the outside diameter of said remaining portion of said outer tubular member, and a plurality of openings formed through said dome-shaped portion and in fluid communication with the lumen of said inner tubular member for allowing fluid exiting said fluid passing orifice to be drawing back through said plurality of openings and the lumen of said inner tubular member;
   (d) drive means disposed at the proximal ends of said outer and inner tubular members for rotating said inner tubular member relative to said outer tubular member at a speed sufficient to cause said cutter member to effectively liquefy said tissue deposits.

2. The surgical device as in claim 1 and further including means associated with said drive means for injecting a flushing liquid between the walls of said inner and outer tubular members, said flushing liquid exiting the lumen of said outer tubular member through said at least one fluid passing orifice.

3. The surgical device as in claim 1 including means associated with said drive means for aspirating liquids through said plurality of openings in said distal end portion of said cutter member, through the lumen of said single inner tubular member and out the proximal end of said inner tubular member as said inner tubular member is being rotated to liquefy said tissue deposits.

4. The surgical device as in claim 1 wherein said drive means comprises:
   (a) a rigid tubular housing having a plug disposed in the distal end thereof;
   (b) a fitting extending through said plug and joined to said proximal end of said outer tubular member;
   (c) a rotary union including
      (i) an outer tubular sleeve keyed to and sealingly fitted within said rigid tubular housing;
      (ii) a hollow manifold member journaled for rotation within said outer tubular sleeve and including an annular recess formed between said manifold member and said tubular sleeve, said recess being in fluid communication with the interior of said hollow manifold;
   (d) means coupling said manifold member to said proximal end of said inner tubular member;
   (e) motor means contained within said rigid tubular housing, the shaft of said motor means coupled to said manifold member to rotate same within said outer tubular sleeve; and
   (f) a fluid port extending through said housing and said tubular sleeve communicating with said annular recess.

5. The surgical device as in claim 4 wherein said motor means is air driven.

6. The surgical device as in claim 1 and further including an annular spacer joining said distal end of said inner tubular member to said tubular portion of said cutter member.

7. The surgical device as in claim 1 wherein said plurality of openings in said dome-shaped distal end portion of said cutter member define a radially disposed arcuate loop projecting longitudinally outward from the distal end of said tubular portion of said cutter member.

8. The surgical device as in claim 1 wherein the total area of said plurality of openings is generally equal to or greater than the cross-sectional area of the lumen of said inner tubular member.

9. The surgical device as in claim 1 wherein said speed is about 30,000 rpm.

* * * * *